(12) United States Patent
Liao et al.

(10) Patent No.: US 10,047,414 B2
(45) Date of Patent: Aug. 14, 2018

(54) METHOD OF REFINING OF SCANDIUM OXIDE FROM CONCENTRATES USING SOLVENT EXTRACTION

(71) Applicant: BLOOM ENERGY CORPORATION, Sunnyvale, CA (US)

(72) Inventors: Lunzhi Liao, San Jose, CA (US); Christopher Jeffrey Hartley, San Francisco, CA (US); Justin McAllister, Sunnyvale, CA (US); Andrew Sarmiento, Daly City, CA (US)

(73) Assignee: BLOOM ENERGY CORPORATION, Sunnyvale, CA (US)

( * ) Notice: Subject to any disclaimer, the term of this patent is extended or adjusted under 35 U.S.C. 154(b) by 83 days.

(21) Appl. No.: 15/041,332

(22) Filed: Feb. 11, 2016

(65) Prior Publication Data
US 2017/0233849 A1   Aug. 17, 2017

(51) Int. Cl.
| | | |
|---|---|---|
| C22B 59/00 | (2006.01) | |
| C22B 34/14 | (2006.01) | |
| C22B 3/44 | (2006.01) | |
| C07C 55/07 | (2006.01) | |

(52) U.S. Cl.
CPC ............. C22B 59/00 (2013.01); C07C 55/07 (2013.01); C22B 3/44 (2013.01); C22B 34/14 (2013.01)

(58) Field of Classification Search
CPC .................................................. C22B 59/00
See application file for complete search history.

(56) References Cited

U.S. PATENT DOCUMENTS

| | | | | |
|---|---|---|---|---|
| 3,288,570 A * | 11/1966 | Henrickson | .......... | C01G 39/003 423/15 |
| 3,323,865 A * | 6/1967 | Michener, Jr. | .......... | C01F 7/748 210/638 |
| 3,658,466 A * | 4/1972 | Otsuka | ................ | C01G 25/003 423/70 |
| 2012/0204680 A1* | 8/2012 | Duyvesteyn | .......... | C22B 3/0005 75/743 |
| 2013/0278658 A1* | 10/2013 | Metcalfe | ................ | B41J 2/2139 347/14 |
| 2014/0193317 A1 | 7/2014 | Hartley et al. | | |
| 2015/0104361 A1* | 4/2015 | Boudreault | ............... | C22B 3/42 423/21.5 |

FOREIGN PATENT DOCUMENTS

| | | | |
|---|---|---|---|
| AU | 2013278658 A1 * | 1/2015 | |
| JP | 11209831 A * | 8/1999 | |

* cited by examiner

*Primary Examiner* — Melissa S Swain
(74) *Attorney, Agent, or Firm* — The Marbury Law Group PLLC

(57) ABSTRACT

A method of selectively removing impurities from a scandium-containing feed solution includes contacting an aqueous scandium-containing solution with an organic solvent stream containing an extractant, thereby forming a loaded organic solvent stream containing the impurity or impurities while leaving the scandium in the raffinate. The aqueous stream containing the scandium is washed, diluted and has inorganic salts added before being contacted with a second organic solvent stream to extract the scandium selectively, and followed by stripping the scandium from the scandium-containing loaded organic extractant stream by adding oxalic acid to the loaded organic extractant stream to form scandium oxalate.

11 Claims, 2 Drawing Sheets

METHOD OF REFINING OF SCANDIUM OXIDE FROM CONCENTRATES USING SOLVENT EXTRACTION

FIELD OF THE INVENTION

The present invention relates generally to selectively recovering scandium from extractive metallurgy waste, and more particularly to extracting and recovering scandium from waste acid streams generated from titanium processing.

BACKGROUND

Due to limitations in mining and availability, scandium is currently only produced in small quantities. While the element occurs in many ores, it is only present in trace amounts; there are no known, easily-extractable deposits of minerals containing high scandium content. Currently, only a few mines produce scandium, and in each case it is made as a byproduct from the extraction of other elements and sold as scandium oxide.

In particular, scandium has gained importance for the use of scandium-stabilized zirconia as a high efficiency electrolyte in solid oxide fuel cells. Applications of scandium also include use of scandium oxide ($Sc_2O_3$) to make high-intensity discharge lamps, and scandium-aluminum alloys that are used for minor aerospace industry components, baseball bats, and bicycle frames. As commercial uses for scandium continue to expand, there exists the need for the development of improved methods to selectively recover scandium from readily available sources.

SUMMARY OF THE INVENTION

An embodiment relates to a method of selectively removing scandium from a scandium-containing feed solution including contacting an aqueous scandium-containing solution with a second organic solvent stream comprising a second extractant, thereby forming a scandium-containing loaded organic solvent stream having at least a portion of the scandium from the scandium-containing solution and stripping the scandium from the scandium-containing loaded organic extractant stream by adding oxalic acid to the loaded organic extractant stream to form scandium oxalate.

Another embodiment relates to a method of selectively removing scandium from an aqueous scandium-containing feed solution including selectively removing zirconium from the aqueous scandium-containing solution by contacting the aqueous scandium-containing solution with a first organic solvent stream comprising a first extractant, the first extractant comprising an amine compound and selectively removing scandium from the aqueous scandium-containing solution after the step of selectively removing zirconium by contacting the aqueous scandium-containing solution with a second organic solvent stream comprising a second extractant to form a scandium-containing loaded organic solvent stream, the second extractant comprising an organo-phosphorous compound and stripping the scandium from the scandium-containing loaded organic extractant stream by forming scandium oxalate.

An embodiment relates to a method of selectively removing a metal from an aqueous feed solution including selectively removing zirconium from the aqueous feed solution using a first organic solvent and stripping the zirconium from the first organic solvent with an aqueous HCl solution.

BRIEF DESCRIPTION OF THE DRAWINGS

The accompanying drawings, which are incorporated herein and constitute part of this specification, illustrate exemplary aspects of the invention. Together with the general description given above and the detailed description given below, the drawings serve to explain features of the invention.

DETAILED DESCRIPTION

Figure 1A:
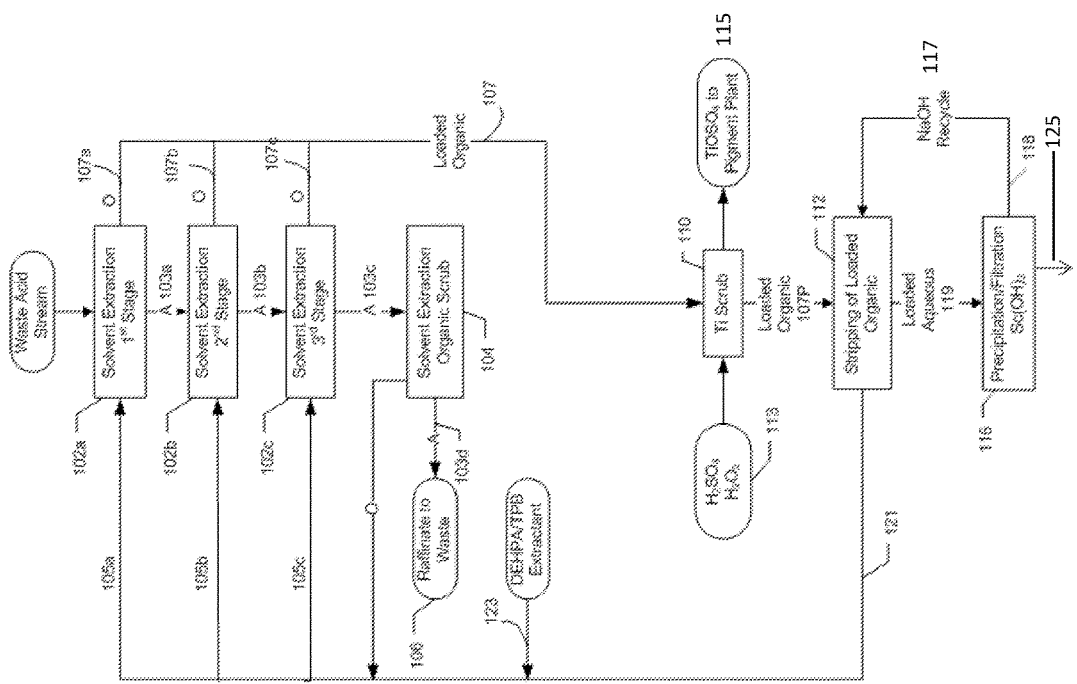
FIG. 1A is a portion of a process flow diagram illustrating an overview of the steps in a method of refining of scandium oxide from concentrates using solvent extraction according to an embodiment.

As used herein, selective removal of an ion or compound generally refers to methods to facilitate the removal of the ion or compound from solutions. As used herein, the selective removal of scandium generally refers to methods to facilitate the removal of scandium (III) ions ($Sc^{3+}$) or scandium-containing compounds from a solution.

As used herein, solvent extraction refers to extracting a substance from one liquid phase (e.g., an aqueous solution) into a different liquid phase (e.g., an organic solvent) based on the relative solubility of the substance in each of the phases.

As used herein, titanium processing refers to extraction or refinement of titanium products, such as titanium dioxide ($TiO_2$) (e.g., by the sulfate process or chloride process), titanium sponge, and/or other titanium products for commercial use from titanium-containing ore. For example, titanium dioxide is commonly extracted from ilmenite using the sulfate method, which produces a waste stream containing dilute sulfuric acid. Another example is the extraction of titanium dioxide from rutile or leucoxene using the chloride method, which produces a waste stream containing hydrochloric acid. In an embodiment, the waste stream (e.g., liquor) from titanium dioxide processing may be hydrolytic solution (i.e., dissolved ions in solution) that contains approximately 15-20 mg/L scandium, with other impurities such as zirconium (Zr), titanium (Ti), iron (Fe) and silicon dioxide ($SiO_2$), In a preferred embodiment, scandium may be directly extracted from the effluent waste liquor from titanium dioxide processing. The embodiments described herein are equally applicable to artificially prepared waste streams that simulate the waste liquor from titanium processing, and to other salt solutions.

Scandium oxide, and more particularly scandium (III) oxide, is described herein as the end product of the various embodiment methods. However, scandium(III) oxide is given merely as an example, and the methods described herein may be used in the production of other useful products, including, but not limited to, non-stoichiometric scandium oxide, scandium(III) chloride ($ScCl_3$), scandium (III) hydroxide ($Sc(OH)_3$), and scandium(III) oxalate ($Sc_2(C_2O_4)_3$). These products are collectively referred to herein as "scandium compound end products".)

Methods for the selective recovery of scandium, e.g., scandium compound end products, for example, in the form of scandium oxide from titanium processing waste streams are provided. The steps of the various embodiments may include: solvent extraction (e.g., cross-current solvent extraction) to load at least one stage (e.g., multiple stages) of an organic phase with scandium ions (e.g., $Sc^{3+}$) from a solution; stripping scandium ions from the organic phase; precipitation of a scandium oxalate product from the filtrate; and drying and calcination a product containing scandium oxide (e.g., $Sc_2O_3$). According to the preferred embodiments, byproducts may be recycled back for use in different steps of the process, or may be converted back into a starting reactant for use in a different step of the process.

Figure 1B:
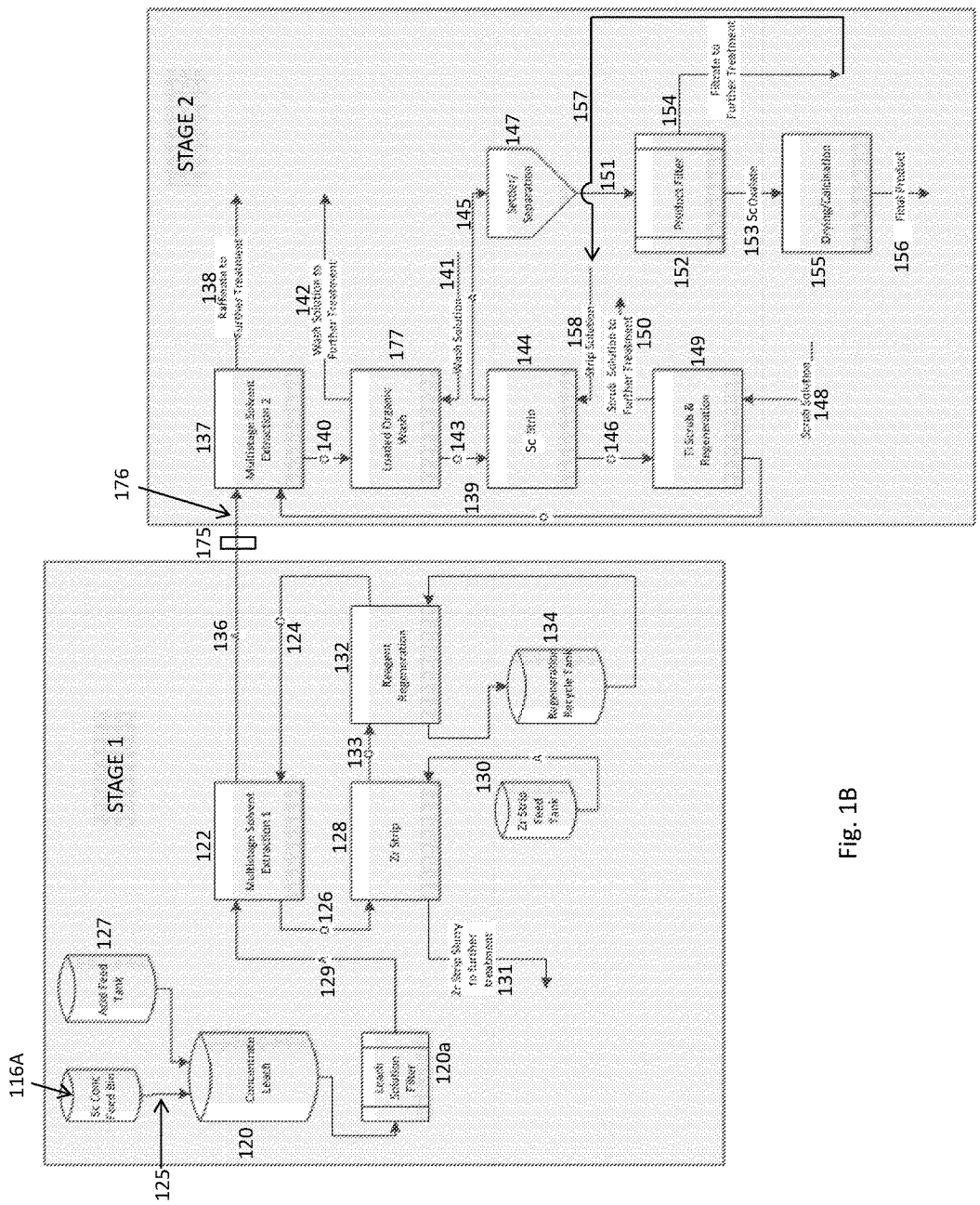
FIG. 1B is another portion of the process flow diagram illustrating additional steps that follow the steps in the method of the embodiment of FIG. 1A.

A method for the selective recovery of scandium from a waste acid stream according to an embodiment is illustrated in FIGS. 1A and 1B. In method 100, scandium may be removed in a multi-stage cross-current solvent extraction process from a waste liquor generated during titanium dioxide (e.g., $TiO_2$) refinement by the sulfate method.

In the various embodiments, cross-current solvent extraction is performed by feeding a scandium-containing stream and a solvent stream into an extraction unit. In preferred embodiments, the scandium-containing stream may be an aqueous phase, i.e., a waste acid liquor stream containing scandium ions, and the solvent stream may be an organic phase.

In a preferred embodiment, cross-current solvent extraction may be performed as a multistage process using a cross-current array. A multistage cross-current array may contain multiple extraction units, for example two to six, such as three extraction units in series. In an embodiment, the extraction units in an array may be mixing tanks or settlers, or mixer-settler units. In another embodiment, extraction units may be centrifugal extractors that mix and separate in the same unit.

In steps 102a-102c, a waste acid stream 101 containing many species in solution, including scandium, may be contacted and mixed with an extractant and an organic liquid at a phase ratio of 1:2 to 1:50, such as 1:25, organic to aqueous (O:A). The organic liquid may be, for example, a high flash point kerosene (e.g., laboratory grade kerosene) or another organic with similar properties (e.g., hexane). In a preferred embodiment, an extractant is also mixed with the waste acid stream and the organic phase. The extractant may be one of a number of commercially available reagents. Examples of such extractants may include, but are not limited to bis(2 ethylhexyl) hydrogen phosphate (DEHPA) (CAS Number 4971-47-5), and tributyl phosphate (TBP) (CAS Number 126-73-8).

The extractant reacts with a portion of the scandium ions in the aqueous phase to form a Sc-extractant complex that is more soluble in the organic liquid than in the aqueous phase. In a preferred multistage cross-current process, the aqueous raffinate 103a, 103b from one extraction unit in steps 102a-102c is fed to the next unit as the aqueous feed, while multiple cross-current streams of the barren (i.e., fresh or unloaded) organic phase 105a-105c are provided to extraction units to contact the aqueous feed, without feeding the loaded organic into the next extraction unit. Thus, barren organic phase is provided to each unit, while the aqueous phase flows from one unit to the next in series in the cross-current extraction process. Each successive extraction stage removes a portion of the remaining scandium ions in the aqueous phase into the organic phase 107a-107c. In a preferred embodiment, solvent extraction may include three cross-current stages, steps 102a-102c. However, other embodiments may include more than three stages, or may include fewer than three stages. In contrast, in a counter-current extraction process, the loaded organic phase is provided from one extraction unit to the next unit in series in an opposite direction to the aqueous phase flow between the units.

Thus, in an embodiment, the scandium-containing feed solution 101 is contacted with a barren first solvent stream 105a in a first stage 102a. The first solvent stream 105a is loaded with at least a portion of the scandium from the feed solution. The loaded first solvent 107a is separated from the remaining scandium-containing feed solution 103a from the first stage 102a.

The first stage is followed by contacting the remaining scandium-containing feed solution 103a from the first stage 102a with a barren second solvent stream 105b in a second stage 102b. The second solvent stream 105b is loaded with at least a portion of the scandium from the remaining scandium-containing feed 103a from the first stage 102a. The loaded second solvent 107b is separated from remaining scandium-containing feed solution 103b from the second stage 103b.

Then, in a third stage 102c, the remaining scandium-containing feed solution 103b from the second stage 102b is contacted with a barren third solvent stream 105c. The third solvent stream 105c is loaded with at least a portion of the scandium from the remaining scandium-containing feed 103b from the second stage 102b. The loaded third solvent 107c is separated from the remaining scandium-containing feed solution 103c from the third stage 102c.

This embodiment may include more than three stages described above. The first, second and third stages 102a-102c in this embodiment may be performed respectively in first, second, and third extraction units, connected in series to form a cross-current array.

At the end of steps 102a-102c, the spent aqueous solution 103c may be scrubbed using, for example, a dual media filter or a coalescer, to recover any organic phase that was carried through the extraction, step 104. The aqueous raffinate may be collected, for example, into a waste holding tank, step 106. Any recovered organic phase can be recycled so that it can be used in steps 105a-105c.

The cumulative loaded organic phase 107 from steps 102a-102c is then purified in a series of scrubbing steps. The scrubbing steps may also be conducted using a cross current process. Preferably, a zirconium scrub step may be omitted between steps 102C and 110.

In step 110, the loaded organic 107 from steps 102a-102c may be provided to a titanium scrubbing process. In an example embodiment, sulfuric acid (e.g., 0.5-5M $H_2SO_4$) and hydrogen peroxide (e.g., 2-10%, e.g., 5% $H_2O_2$) 113 may be used as scrubbing agents to remove titanium impurities 115. Other impurities that may be removed by further optional scrubbing stages (not shown for clarity in FIG. 1A) may include, for example, iron (Fe) and manganese (Mn).

The spent scrubbing agents containing the impurities 111, 115 from step 110 may also contain recoverable, usable compounds. For example, one of the compounds that may be present in the spent sulfuric acid and hydrogen peroxide used for titanium scrubbing in step 110 is titanium oxysulfate ($TiOSO_4$) 115. Titanium oxysulfate, which can be used as a mordant in dyeing processes, may be recovered from the spent scrubbing agent and used and/or sold for use in a pigment plant.

In step 112, a strip solution 117 may be added to the purified loaded organic phase 107P to unload scandium. The strip solution may be, for example, a sodium hydroxide (NaOH) solution. $Sc^{3+}$ ions may be unloaded from the organic phase 107P and into an aqueous phase 119 with $Na^+$ and $OH^-$, from which $Sc(OH)_3$ may precipitate out of solution. Stripping scandium from the organic phase 107P using a NaOH strip solution may proceed according to the following reaction:

$$HSc(SO_4)_2 \cdot xHR + 8NaOH \rightarrow Sc(OH)_3\downarrow + 2Na_2SO_4 + xNaR \quad \text{(eq. 2)}.$$

In an embodiment, the unloaded organic (i.e., barren organic 121) liquid may be recycled back to the extraction units to be incorporated in the organic phase 105a-105c for the solvent extraction stages in steps 102a-102c. Extractant 123 can be added to barren organic 121 and recovered organic from step 104 to form the organic phase 105a-105c. $Sc(OH)_3$ may be separated from the aqueous solution 119 using any suitable techniques. In an example embodiment, $Sc(OH)_3$ precipitate 125 may be separated from the aqueous phase 119 in a clarifier. In another embodiment, a centrifuge may be used to separate the precipitated $Sc(OH)_3$ 125 from solution 119. In a preferred embodiment, the aqueous solution 119 containing $Sc(OH)_3$ precipitate may be fed into a filter (e.g., a vacuum filter) to produce a filter cake of $Sc(OH)_3$ 125 in step 116. The filtrate solution may be recovered in a tank, and, in step 118, sodium hydroxide 117 may be recycled back to the strip solution used in step 112 to unload scandium ions from the organic phase 107P. In an embodiment, the resulting filter cake may contain, for example, 10-90 wt % $Sc(OH)_3$, thereby yielding 5-50 wt % scandium. The components which make up the remainder of the resulting filter cake may be, for example, residual $TiO_2$, NaOH, iron, calcium and/or rare earth elements.

As illustrated in FIG. 1B, the remaining steps of the method may be grouped in two stages to aid in understanding of the method. The first stage, Stage 1, comprises solvent extraction of zirconium from an aqueous solution of the filter cake produced in step 116. The second stage, Stage 2, comprises solvent extraction of scandium from the raffinate of Stage 1. The details of Stage 1 and Stage 2 are as follows.

In step 120 of Stage 1, the filter cake 125 formed in step 116 may be provided from a concentrated scandium feed bin 116A into a leaching tank together with an acid 127 from an acid feed tank to leach and dissolve the Sc containing filter cake. In an embodiment, a scandium containing concentrate containing 5-50% (w/w) Sc on a dry basis may obtained from a stream such as spent acid from a $TiO_2$ pigment plant. The leach solution may then be filtered in step 120a, producing an outflow filtrate solution 129 with scandium ions as well as impurity ions such as Zr and Ti. In an embodiment, the leaching acid 127 may be, but is not limited to, hydrochloric acid (HCl) or sulfuric acid ($H_2SO_4$) to produce an acidic aqueous solution 129 at pH 0.1-1.0 containing up to 10 g/L Sc. In an embodiment, the leach solution may include 5-10 g/L of Sc, 1-5 g/L of Zr, 1-5 g/L of Ti, 0.1-0.5 g/L of Fe and 0.1-0.8 g/L of Ca.

In step 122, the acidic aqueous filtrate solution 129 may be contacted with an organic phase 124 in a zirconium solvent extraction process. The organic phase 124 may be an organic extractant comprising an amine extractant at 5-20% (v/v), such as 10% (v/v) concentration, in an organic solvent, such as high flash point kerosene. The extractant may be any compound that complexes with (i.e. binds to) Zr from the aqueous phase and returns into the organic phase. In a preferred embodiment, the extractant has an amine functional group and C5-C12 carbon chain. Zr binds to the amine group. Preferably, the extractant does not bind to/complex with Sc. Preferably, the extractant is a straight chain amine with C8-C10 in the alkyl group, (e.g. BASF Alamine® 336). In an embodiment, the organic phase may include a diluent and/or a modifier at 5-20% (v/v), such as 10% (v/v) concentration. The modifier is any compound that improves transport across the boundary between the aqueous and organic phases and aids in disengagement of the phases. That is, the modifier helps drops of organic phase located in the aqueous phase to coalesce into the organic phase. Example modifiers include long chain alcohols, e.g. with a C8-C15 carbon chain. Suitable alcohols include both straight and branched alcohols. In a preferred embodiment, the alcohol comprises a carbon chain that includes 12 carbons, such as tridecyl alcohol (e.g., Exxal™ 13). The diluent may be any material that improves the solubility of the organic extractant in the organic phase, such as kerosene or a dearomatized hydrocarbon fluid (e.g., Exxsol™ D80). In an embodiment, the organic phase may have a composition of 10-20% (v/v) amine, 5-15% (v/v) modifier and a balance of kerosene (65-85% (v/v)).

The solvent extraction in step 122 may be carried out, for example, in any suitable solvent extraction plant using one or more mixer-settlers in single or multi stage (such as 2-5, such as 3 stages) process. As a result of step 122, the organic phase 124 may be loaded with zirconium ions from the filtrate solution 129, forming loaded organic phase 126. In an embodiment, step 122 results in removal of the Zr (e.g. 0.1 g/L or less Zr remains in the raffinate) from the filtrate solution 129 with no significant loss (e.g. less than 1% (M/M)) of Sc.

In step 128, the Zr can be stripped from the loaded organic phase 126 with a strong acid 130 (e.g. 2-6M, such as 4M HCl) from an acid feed tank to allow recovery of pure $ZrOCl_2$ or $ZrO_2$ 131 from the acidic Zr strip slurry or solution, if desired. The remaining organic phase extractant 133 from step 128 may be regenerated in step 132 by treating it with an alkaline solution 134 (e.g. 40-100 g/L $Na_2CO_3$, or 20-100 g/L NaOH) from a recycle tank to reactivate the amine containing organic phase 124 to recycle it to step 122 of Stage 1.

The aqueous raffinate 136 may be diluted by adding demineralized water, such as to a concentration of 2-4 g/L, such as 3g Sc/L of water in step 175. Additionally, $MgSO_4$ may be added in step 175 to the aqueous raffinate 136, such as at about 0.5M concentration, to aid separation of the organic phase from the aqueous phase after mixing in the second solvent extraction 137. In an embodiment, the diluted aqueous raffinate 176 provided to step 137 includes 1.0-5.0 g/L of Sc, 0.5-2.5 g/L of Ti, 0.01-0.10 g/L of Zr, 0.05-0.25 g/L of Fe, 0.1-0.5 g/L of Ca and 6.0-20 g/L of Mg. The pH may be 0.3-1.0.

In stage 2, in the second solvent extraction 137, Sc from the diluted aqueous raffinate 176 is selectively extracted into an organic phase 139. The organic phase 139 comprises an organophosphorus extractant (e.g. a dialkyl phosphinic acid extractant, such as Cytec Cyanex 272®, which comprises bis(2,4,4-trimethylpentyl) phosphinic acid) at 10-20% (v/v) concentration to form a loaded organic phase 140 from step 137. In an embodiment, the organic phase 139 also includes a modifier (e.g. tri-butyl phosphate TBP) at 5-20% (v/v), such as 10% (v/v) concentration in a diluent (e.g. Exxsol D80 or kerosene). The aqueous raffinate 138 (e.g. sulfuric acid solution) from the second solvent extraction 137 may be further treated for recycle, i.e. returned to the extraction plant for recovery of any Sc remaining in the aqueous raffinate 138. The loaded organic phase 140 from step 137 includes Ti and Sc which are complexed to the organic extractant.

The loaded organic phase 140 is then washed in step 177, such as with 15 g/L NaCl solution 141, to remove any entrained aqueous phase along with iron, calcium and other un-complexed metals from the second solvent extraction 137, forming a washed loaded organic phase 143. The loaded wash solution 142 may be further processed for reuse (e.g. to remove Ca, Fe, etc.).

The complexed scandium is stripped from the washed loaded organic phase 143 in a Sc strip step 144. The Sc is stripped by contacting washed loaded organic phase 143 with a strip solution 158 comprising, for example, 75-150 g/L, such as 100 g/L oxalic acid solution at 40-80° C. (typically 60° C.) to precipitate the Sc as scandium oxalate ($Sc_2(C_2O_4)_3$) in an aqueous suspension or mixture 145. In an embodiment, after mixing the washed loaded organic phase 143 with the strip solution 158, the acidic aqueous mixture 145 is provided to a settler/separator 147. The settled output 151 from the settler 147 is then provided to a filter 152 to separate the scandium oxalate 153 from the oxalic acid containing filtrate 154. The filtrate 154 may be recycled via a conduit 157 for further use as a strip solution 158. This stream may be monitored for buildup of impurities (e.g. Zr) and periodically a bleed stream may be treated to reduce the level of these in the circuit.

In step 155, the $Sc_2(C_2O_4)_3$ in the filtered scandium oxalate precipitate 153 may be dried of excess moisture and calcined (i.e., heated to convert $Sc_2(C_2O_4)_3$ to $Sc_2O_3$) at 700-800 degrees Celsius to obtain a scandium compound end product 156 (e.g., a scandium oxide solid composition) that has a composition of at least 99 wt %, such as around 99 to 99.9 wt % scandium oxide.

In a Ti scrub and organic solution regeneration step 149, the complexed Ti containing stripped organic solution 146 from step 144 is scrubbed to remove the co-extracted Ti by treating the stripped organic solution 146 with an aqueous solution 148, e.g. 400-600 g/L, such as 500 g/L, $H_2SO_4$ and 2-5% (v/v), such as 3% (v/v) $H_2O_2$, to remove the Ti. The resulting organic phase 139 from step 149 can be recycled to the second solvent extraction step 137. The loaded scrub solution 150 may be further processed for reuse (e.g., to remove Ti).

As is understood in the art, not all equipment or apparatuses are shown in the figures. For example, one of skill in the art would recognize that various holding tanks and/or pumps may be employed in the present method.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the steps as a sequential process, many of the steps can be performed in parallel or concurrently.

Any reference to claim elements in the singular, for example, using the articles "a," "an" or "the" is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

The invention claimed is:

1. A method of selectively removing scandium from a scandium-containing feed solution, comprising:
   selectively removing zirconium from the aqueous scandium-containing solution by contacting an aqueous scandium-containing solution with a first organic solvent stream comprising a first extractant;
   providing $MgSO_4$ and adding the $MgSO_4$ to the aqueous scandium-containing solution after contacting the aqueous scandium-containing solution with the first organic solvent stream;
   contacting the aqueous scandium-containing solution with a second organic solvent stream comprising a second extractant after adding the $MgSO_4$, thereby forming a scandium-containing loaded organic solvent stream having at least a portion of the scandium from the scandium-containing solution; and
   stripping the scandium from the scandium-containing loaded organic extractant stream by adding oxalic acid to the loaded organic extractant stream to form scandium oxalate and a stripped organic extractant stream.

2. The method of claim 1, wherein the second extractant comprises an organophosphorus compound.

3. The method of claim 1, wherein the second organic solvent stream further comprises a modifier and a diluent.

4. The method of claim 1, further comprising calcining the scandium oxalate to form $Sc_2O_3$.

5. The method of claim 1, further comprising scrubbing the stripped organic extractant stream after stripping the scandium to remove titanium from the stripped organic extractant stream.

6. The method of claim 1, wherein the first extractant comprises an amine compound, and wherein the step of selectively removing zirconium occurs prior to contacting the aqueous scandium-containing solution with the second organic solvent stream.

7. The method of claim 6, further comprising stripping the zirconium from the first organic solvent with an aqueous chloride solution.

8. The method of claim 7, wherein the aqueous chloride solution comprises an aqueous HCl solution.

9. The method of claim 5, wherein scrubbing the stripped organic extractant stream to remove titanium from the stripped organic extractant stream comprises using sulfuric acid and hydrogen peroxide to remove the titanium.

10. The method of claim 1, wherein the second extractant comprises a dialkyl phosphinic acid extractant.

11. The method of claim 1, wherein the second extractant comprises bis(2,4,4-trimethylpentyl) phosphinic acid.

* * * * *